United States Patent
Kvam et al.

(10) Patent No.: US 9,040,679 B2
(45) Date of Patent: *May 26, 2015

(54) METHODS AND COMPOSITIONS FOR EXTRACTION AND STORAGE OF NUCLEIC ACIDS

(71) Applicant: General Electric Company, Schenectady, NY (US)

(72) Inventors: Erik Leeming Kvam, Niskayuna, NY (US); Bing Li, Troy, NY (US); Brian Christopher Bales, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/968,497

(22) Filed: Aug. 16, 2013

(65) Prior Publication Data

US 2013/0338351 A1    Dec. 19, 2013

Related U.S. Application Data

(63) Continuation-in-part of application No. 13/460,076, filed on Apr. 30, 2012, and a continuation-in-part of application No. 13/721,948, filed on Dec. 20, 2012.

(51) Int. Cl.
*C12N 15/10* (2006.01)
*B01J 20/24* (2006.01)

(52) U.S. Cl.
CPC .............. *B01J 20/24* (2013.01); *C12N 15/1006* (2013.01); *C12N 15/1003* (2013.01)
USPC ..................................................... 536/25.42

(58) Field of Classification Search
USPC ..................................................... 536/25.42
See application file for complete search history.

(56) References Cited

U.S. PATENT DOCUMENTS

| | | | |
|---|---|---|---|
| 4,540,506 A | 9/1985 | Jacobson et al. | |
| 5,173,422 A | 12/1992 | Knowles et al. | |
| 5,756,126 A | 5/1998 | Burgoyne | |
| 5,807,527 A | 9/1998 | Burgoyne | |
| 5,939,259 A | 8/1999 | Harvey et al. | |
| 5,981,218 A * | 11/1999 | Rio et al. ..................... | 435/69.1 |
| 6,168,922 B1 | 1/2001 | Harvey et al. | |
| 6,294,203 B1 | 9/2001 | Burgoyne | |
| 6,528,641 B2 | 3/2003 | Lader | |
| 6,602,718 B1 | 8/2003 | Augello et al. | |
| 6,776,959 B1 | 8/2004 | Helftenbein | |
| 6,794,140 B1 | 9/2004 | Goldsborough | |
| 6,867,290 B2 | 3/2005 | Goldsborough | |
| 7,163,793 B2 | 1/2007 | Kudlicki et al. | |
| 7,244,568 B2 | 7/2007 | Goldsborough | |
| 7,250,270 B2 | 7/2007 | Goldrick et al. | |
| 7,282,371 B2 | 10/2007 | Helftenbein | |
| 7,589,184 B2 | 9/2009 | Hogan et al. | |
| 8,025,850 B2 | 9/2011 | Chan | |
| 8,048,681 B2 * | 11/2011 | Yamashita et al. ............ | 436/111 |
| 8,088,576 B2 | 1/2012 | Gumbrecht et al. | |
| 8,158,357 B2 | 4/2012 | Birnboim et al. | |
| 2001/0039010 A1 | 11/2001 | Burgoyne | |
| 2002/0146696 A1 | 10/2002 | Burgoyne et al. | |
| 2003/0143566 A1 | 7/2003 | Helftenbein | |
| 2004/0009496 A1 | 1/2004 | Eiblmaier et al. | |
| 2004/0126783 A1 | 7/2004 | Bortolin et al. | |
| 2005/0123965 A1 * | 6/2005 | Yamashita et al. ................ | 435/6 |
| 2006/0099567 A1 | 5/2006 | Muller-Cohn et al. | |
| 2006/0147918 A1 | 7/2006 | Goldsborough | |
| 2007/0117173 A1 | 5/2007 | Levison et al. | |
| 2008/0176209 A1 | 7/2008 | Muller et al. | |
| 2008/0262097 A1 | 10/2008 | Eady et al. | |
| 2009/0053704 A1 | 2/2009 | Novoradovskaya et al. | |
| 2009/0162924 A1 | 6/2009 | Birnboim | |
| 2009/0208919 A1 | 8/2009 | Utermohlen et al. | |
| 2009/0246750 A1 | 10/2009 | Lloyd et al. | |
| 2009/0291427 A1 | 11/2009 | Muller-Cohn et al. | |
| 2010/0173392 A1 | 7/2010 | Davis et al. | |
| 2010/0209957 A1 | 8/2010 | Hogan et al. | |
| 2010/0248363 A1 | 9/2010 | Hogan et al. | |
| 2011/0070585 A1 | 3/2011 | Ollikka et al. | |
| 2011/0081363 A1 * | 4/2011 | Whitney et al. ............ | 424/184.1 |
| 2012/0052572 A1 | 3/2012 | Whitney et al. | |
| 2012/0059160 A1 | 3/2012 | Bitner et al. | |
| 2012/0152743 A1 | 6/2012 | Finehout et al. | |
| 2012/0237939 A1 | 9/2012 | Reed et al. | |
| 2013/0289257 A1 | 10/2013 | Bales et al. | |

FOREIGN PATENT DOCUMENTS

| | | |
|---|---|---|
| EP | 1484111 A1 | 12/2004 |
| EP | 1559784 A2 | 8/2005 |
| EP | 2388312 A1 | 11/2011 |
| WO | 00/66606 A1 | 11/2000 |
| WO | 2007008722 A2 | 1/2007 |
| WO | 2009029433 A2 | 3/2009 |
| WO | 2010132508 A2 | 11/2010 |
| WO | 2011131720 A1 | 10/2011 |
| WO | 2012075471 A1 | 6/2012 |
| WO | 2012113907 A2 | 8/2012 |
| WO | 2013066249 A1 | 5/2013 |

OTHER PUBLICATIONS

Matsubara et al., "Dried blood spot on filter paper as a source of mRNA", Nucleic Acids Research, vol. 20, Issue 8, Apr. 25, 1992, pp. 1998; 1 Page.

Zhang et al., "RNA analysis from newborn screening dried blood specimens", Human Genetics, vol. 89, Issue 3, May 1992, pp. 311-314.

Search Report and Written Opinion from PCT Application No. PCT/US2013/38576 dated Sep. 6, 2013.

(Continued)

*Primary Examiner* — Ganapathy Krishnan
(74) *Attorney, Agent, or Firm* — Eileen B. Gallagher

(57) ABSTRACT

A solid matrix for the extraction, stabilization, and storage of nucleic acids is provided. At least one protein denaturant, and at least one acid or acid-titrated buffer reagent are impregnated in a dry state therein the matrix; and the matrix is configured to provide an acidic pH on hydration. The matrix is configured to extract nucleic acids from a sample and stabilize the extracted nucleic acids, particularly RNA, in a dry format under ambient conditions for a prolonged period of time. Methods for collecting and recovering the nucleic acids stored in the dry solid matrix are also described.

38 Claims, 4 Drawing Sheets

(56) References Cited

OTHER PUBLICATIONS

Tan, et al., "DNA, RNA, and Protein Extraction: The Past and the Present", Journal of Biomedicine and Biotechnology, 2009, pp. 1-10.

Kumar et al. "Inhibition of mammalian ribonucleases by endogenous adenosine dinucleotides", 2003 Biochemical and Biophysical Research Communications 300 pp. 81-86.

Cline, et al. "New Water-Soluble Phosphines as Reductants of Peptide and Protein Disulfide Bonds: Reactivity and Membrane Permeability" 2004 Biochemistry 43: pp. 15195-15203.

Search Report and Written Opinion from PCT Application No. PCT/US2013/065821 dated Jan. 29, 2014.

Li, et al, "Kinetics of RNA degradation by specific base catalysis of transesterification involving the 2'-hydroxyl group" Journal American Chemistry Society, 1999, 121 (23) pp. 5364-5372.

Zale, et al. "Why does ribonuclease irreversibly inactivate at high temperatures?", Biochemistry, 1986, 25 (19) pp. 5432-5444.

Natarajan, et al. "Paper-based archiving of mammalian and plant samples for RNA analysis" BioTechniques, 2000, 29 pp. 1328-1333.

Sambrook, J. et al. "Molecular Cloning: a Laboratory Manual, 2nd edition" Cold Spring Harbor, New York, Cold Spring Harbor Laboratory Press, Dec. 1989, vol. 1, pp. 7.2, 7.3, 7.4 and 7.5.

Ambion Technotes, "Maximize Your RNA Yield: What Yield to Expect", vol. 8, Issue No. 3, pp. 1, 13-14, I, May 18, 2001.

Ambion, "RNAqueousTM-4PCR Instruction Manual passage", RNAqueous-4PCR Instruction Manual, pp. 1-29, Apr. 18, 2002.

PCT Search Report and Written Opinion issued in connection with corresponding Application No. PCT/EP2014/067453 on Dec. 19, 2014.

European Search Report issued in connection with corresponding EP Application No. 13784927.9 on Jan. 29, 2015.

* cited by examiner

METHODS AND COMPOSITIONS FOR EXTRACTION AND STORAGE OF NUCLEIC ACIDS

CROSS REFERENCE TO RELATED APPLICATIONS

This application is a continuation-in-part of U.S. patent application Ser. No. 13/460,076 entitled "Methods and compositions for extraction and storage of nucleic acids", filed Apr. 30, 2012; and U.S. patent application Ser. No. 13/721, 948 entitled "Formulations for nucleic acid stabilization on solid substrates", filed Dec. 20, 2012; which are herein incorporated by reference.

FIELD

The invention relates to solid substrates and methods for ambient extraction and stabilization of nucleic acids from a biological sample in a dry format. Methods for collecting, extracting, preserving, and recovering nucleic acids from the dry solid substrates are also described.

BACKGROUND

Preserving the structural and functional integrity of biomolecules during isolation or purification from a biological sample is essential for various downstream applications. The downstream applications of purified biomolecules may include analyte detection, sensing, forensic, diagnostic or therapeutic applications, sequencing, amplification, and the like. The success of these downstream applications may depend on maintaining the integral structure and function of target biomolecules. Various factors, such as temperature, pressure, pH, chemical or enzymatic hydrolysis, or the presence of contaminants may cause degradation of biomolecules such as DNA, RNA or protein.

RNA is one of the most unstable biomolecules due to chemical self-hydrolysis and enzyme-mediated degradation. The extraction and stabilization of RNA derived from a biological sample is sensitive to a number of environmental factors including, but not limited to, the buffer used to extract or collect the RNA, solution pH, temperature, and particularly the ubiquitous presence of robust ribonucleases (RNases). RNA is typically stored under refrigeration (e.g. 4° C., −20° C., or −80° C.) in both purified and unpurified forms to prevent hydrolysis and enzymatic degradation and thus preserve the integrity of the RNA sample. The methods and articles for extraction and stabilization of RNA under ambient temperatures are desirable in order to avoid the costs and space requirements associated with refrigeration for maintaining the integrity of the RNA samples.

Current methodologies for stabilizing RNA under ambient temperature have focused on deactivating RNases in excess liquid solutions of, for example, detergents, chaotropic compounds, reducing agents, transitional metals, organic solvents, chelating agents, proteases, RNase peptide inhibitors, and anti-RNase antibodies. Additional efforts have focused on chemical modification of RNA to restrict trans-esterification and self-hydrolysis. Dry-state technologies claiming successful collection and preservation of RNA in dry formats typically require that RNA be "pre-purified" and concentrated from a sample prior to storage of the RNA. Other dry-state technologies for the preservation of RNA in dry formats require additional drying facilities (e.g. forced air flow, lyophilization, or heat treatment). These methods are therefore not conducive to direct RNA collection from a sample (e.g., a biological sample) without significant sample processing.

Accordingly, compositions and methods that enable dry-state RNA extraction and stabilization from a biological sample under ambient conditions within a single process-step are needed. Moreover, the ability to store a dried biological sample for a substantial period at ambient temperature and recover intact RNA thereafter for further analysis is highly desirable.

BRIEF DESCRIPTION

One embodiment of a solid matrix comprises at least one protein denaturant, and at least one acid or acid-titrated buffer reagent impregnated therein in a dry state; wherein the matrix is configured to provide an acidic pH upon hydration, extract nucleic acids from a sample and preserve the nucleic acids in a substantially dry state at ambient temperature.

In another embodiment, an RNA extraction matrix comprises a protein denaturant comprising a chaotropic agent, a detergent or combination thereof; and an acid or acid-titrated buffer reagent impregnated therein in a dry state, wherein the matrix is a porous non-dissolvable dry material configured to provide a pH between 2 and 7 upon hydration for extracting RNA and stabilizing the extracted RNA with an RNA Integrity Number (RIN) of at least 4.

In one embodiment, an RNA extraction matrix comprises a protein denaturant comprising a chaotropic agent, a detergent or combination thereof; an acid or acid-titrated buffer reagent; and an RNase inhibitor comprising a triphosphate salt or pyrophosphate salt, impregnated therein in a dry state, wherein the matrix comprises a porous non-dissolvable dry material configured to provide a pH between 2 and 7 upon hydration and stabilize RNA with an RNA Integrity Number (RIN) of at least 4.

One example of a method for extracting and storing nucleic acids from a sample comprises the steps of providing the sample to a dry solid matrix comprising a protein denaturant and an acid or acid titrated buffer reagent; generating an acidic pH upon hydration for extraction of nucleic acids from the sample; drying the matrix comprising the extracted nucleic acids; and storing the extracted nucleic acids on the matrix in a substantially dry state at ambient temperature.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
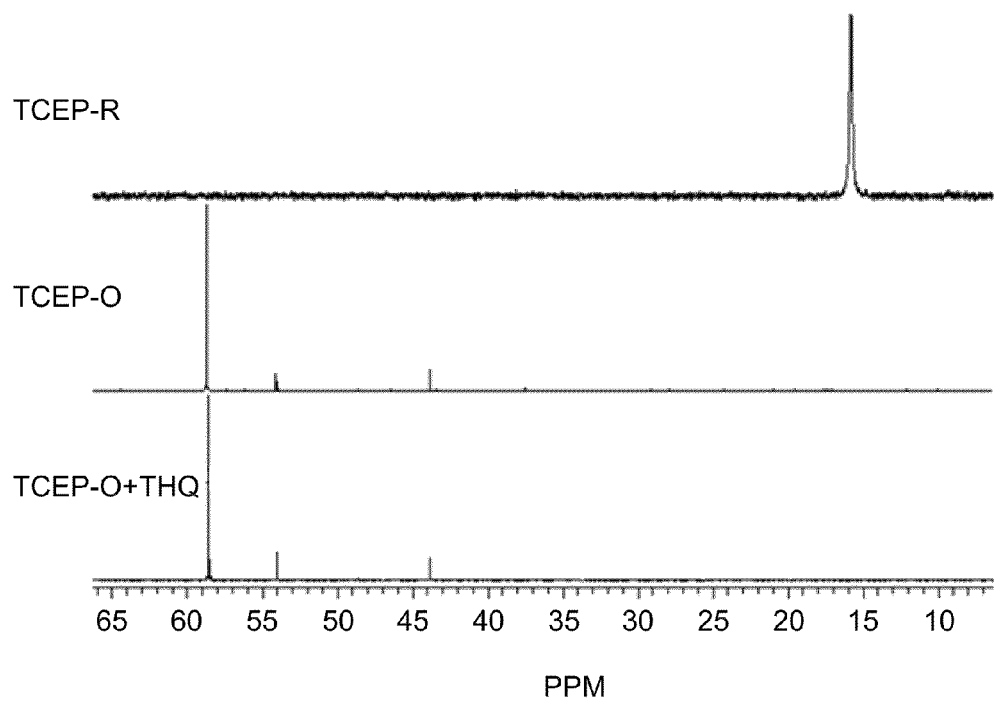
FIG. 1 is a $P^{31}$ NMR profile showing the oxidation of Tris(2-carboxyethyl) phosphine (TCEP) and preparation of TCEP Oxide (TCEP-O).

The embodiments of present invention provide suitable matrices and methods for ambient extraction and preservation of nucleic acids, such as RNA. RNA is generally known as an unstable molecule which is difficult to preserve in an intact form. One or more embodiments of the invention relate to a nucleic acid extraction matrix, wherein the matrix is configured to collect, extract and store nucleic acids from a biological sample for a prolonged period within a single process step, followed by use in various applications. The matrix is configured to store nucleic acids in a substantially dry-state at ambient temperature and substantially retain the integrity of the nucleic acids.

To more clearly and concisely describe the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

The term "nucleic acid" as referred to herein comprises all forms of RNA (e.g., mRNA, miRNA, rRNA, tRNA, piRNA, ncRNA), DNA (e.g. genomic DNA, mtDNA), as well as recombinant RNA and DNA molecules or analogues of DNA or RNA generated using nucleotide analogues. The nucleic acids may be single stranded or double stranded. The nucleic acids may include the coding or non-coding strands. The term also comprises fragments of nucleic acids, such as naturally occurring RNA or DNA which may be recovered using the extraction methods disclosed. "Fragment" refers to a portion of a nucleic acid (e.g., RNA or DNA).

The term "biological sample" as referred to herein includes, but is not limited to, blood, serum, tissue, and saliva obtained from any organism, including a human. Biological samples may be obtained by an individual undergoing a self-diagnostic test (e.g., blood glucose monitoring) or by a trained medical professional through a variety of techniques including, for example, aspirating blood using a needle or scraping or swabbing a particular area, such as a lesion on a patient's skin. Methods for collecting various biological samples are well known in the art. The term "sample" includes biological samples as defined above, but also includes, for example, tissue cultured cells and purified nucleic acids.

The term, "reducing agents" as referred to herein include any chemical species that provides electrons to another chemical species. A variety of reducing agents are known in the art. Exemplary reducing agents include dithiothreitol (DTT), 2-mercaptoethanol (2-ME), and tris(2-carboxyethyl)phosphine (TCEP). Moreover, any combination of these or other reducing agents may be used. In particular embodiments, the reducing agent is TCEP.

The term "buffer" as used herein includes, for example, 2-Amino-2-hydroxymethyl-propane-1,3-diol (Tris), 2-(N-morpholino) ethanesulfonic acid (MES), 3-(N-morpholino) propanesulfonic acid (MOPS), citrate buffers, 4-(2-hydroxyethyl)-1-piperazineethanesulfonic acid (HEPES), and phosphate buffers. This list of potential buffers is for illustrative purposes only. The pH of the buffer selected for use in the compositions and methods disclosed herein is typically acid-titrated in the range of 2 to 7.

One or more embodiments of a solid matrix comprise at least one protein denaturant and at least one acid or acid-titrated buffer reagent impregnated in a dry state therein, wherein the matrix is configured to provide an acidic pH upon hydration. The matrix is also configured to extract nucleic acids from a sample and preserve the nucleic acids in a substantially dry state at ambient temperature. As used herein, the term "substantially dry state" refers to further drying the sample to have approximately less than 2% of water content.

Solid matrices for the extraction and storage of nucleic acids from a sample comprise at least one acid or acid-titrated buffer and a protein denaturant in a dry state. The term "matrix" is interchangeably used herein as "extraction matrix". The term "solid matrix" as used herein refers to a non-dissolvable matrix. The matrix enables collection, extraction and storage of nucleic acids without solubilizing the matrix material. The solid matrix includes, but is not limited to, materials such as cellulose, cellulose acetate, nitrocellulose, glass fibers or combinations thereof. "Incorporation" of the compositions into the matrix includes, but is not limited to, the "dipping" procedure described below. In some embodiments, such methods accomplish incorporation of the composition into the dry solid matrix. Following incorporation of the composition into the dry solid matrix, the solid matrix is dried using any appropriate method.

As noted, the solid matrix comprises the composition in a dry state and also preserves the extracted nucleic acids under dry conditions. The use of a dry solid matrix for extraction and storage is advantageous over liquid-based extraction, because the dry matrix ensures minimal volumetric dilution of the sample applied to the matrix. One of skill in the art would appreciate that liquid-based extraction dilutes the concentration of the sample in an excess volume of stabilizing reagent. Use of dry solid matrix for collecting, extracting, and preserving a sample maintains the concentration of the sample and eliminates issues, such as sample degradation, that are related to improper dilution of sample in a liquid preservative. In addition, the solid matrix comprises a fixed composition of the dry reagents, which enables efficient extraction of nucleic acids, such as RNA, upon hydration, followed by stabilization of the extracted RNA at ambient temperature.

The terms "ambient condition" or "ambient temperature" are interchangeably used hereinafter. As used herein, the term "ambient temperature" refers to a temperature in a range between 0° C. to 60° C. In one or more embodiments, the ambient temperature is room temperature. In some embodiments, the matrix is configured to store or preserve nucleic acids under ambient temperature in a dried state.

As noted, the solid matrix is configured to store or preserve nucleic acids under dry-state for prolonged period. The term "configured to" or "configured for" is referred to herein as the structure or composition of the matrix that enables the matrix to extract and store nucleic acids for periods of time at ambient temperature. The terms "storage" or "preservation" may be interchangeably used herein with respect to maintaining the extracted nucleic acids in a format suitable for further analysis. More specifically, the nucleic acids may be stored or preserved in a solid nucleic acid extraction matrix, wherein the matrix ensures maintaining the integrity of the molecules.

In some embodiments, the nucleic acid extraction matrix is a solid phase extraction matrix. A matrix, where the solid phase extraction method is used, is referred to herein as a solid phase extraction matrix. Solid-phase extraction (SPE) technology has been leveraged to reduce the extraction times of high purity nucleic acids for sequencing and other applications. The solid phase extraction is an extraction method that uses a solid phase and a liquid phase to isolate one or more molecules of the same type, or different types, from a material. The solid phase extraction matrix is used, for example, to purify a sample upstream of a chromatographic or other analytical method. tone example of the method comprises loading a sample (e.g. a biological sample) onto the solid phase extraction matrix, storing the matrix at ambient temperature to achieve a substantially dry state, and rehydrating the matrix with a suitable buffer to differentially extract RNA from the matrix.

The term "extraction" refers to any method for separating or isolating the nucleic acids from a sample, more particularly from a biological sample. Nucleic acids such as RNA and DNA may be released, for example, by cell-lysis. In one embodiment, nucleic acids may be released during evaporative cell-lysis. In another embodiment, the cells are lysed upon contact with the matrix comprising cell lysis reagents. Contacting a biological sample comprising cells to the matrix results in cell lysis which releases nucleic acids, for example by using FTA™ Elute cellulose papers.

The solid matrix may be porous. In one embodiment, the solid matrix is a porous cellulose paper, such as a cellulose matrix from Whatman™. In one example, the cellulose matrix from Whatman™ comprises 903-cellulose, FTA™ or FTA™ Elute.

In one or more examples, the extraction matrix is impregnated with one or more reagents. As noted, in an example embodiment, the matrix comprises one or more protein denaturants impregnated in a dry state. In one embodiment, the matrix further comprises one or more acids or acid-titrated buffer reagents. In another embodiment, the matrix further comprises one or more reducing agents. In some embodiments, the impregnated reagents comprise lytic reagents, nucleic acid-stabilizing reagents, nucleic acid storage chemicals and combinations thereof.

In some embodiments, the dried reagents impregnated in the matrix are hydrated by adding a buffer, water or a sample. In one embodiment, the impregnated dried reagents are hydrated by a sample, more specifically a biological sample, which is disposed on the matrix for extraction or storage of nucleic acids. In some other embodiments, in addition of a sample, water or buffer is added to hydrate the matrix and reconstitute or activate the reagents embedded in the matrix. In some embodiments, the hydration of the matrix generates an acidic pH on the matrix. In some embodiments, the hydration further results in reconstituting the reagents, such as protein denaturant, acid or acid titrated buffer reagents that are present in a dried form in the matrix.

In one or more embodiments, the matrix comprises a protein denaturant. The protein denaturant may comprise a chaotropic agent or detergent. Without intending to be limited to a particular denaturant, protein denaturants may be categorized as either weak denaturants or strong denaturants depending on their biophysical properties and ability to completely inhibit biological enzyme activity (e.g. RNases). In some embodiments, weak protein denaturants (e.g. detergent) may be used for lysing cells and disrupting protein-protein interactions without denaturing nucleic acids. In further embodiments, use of strong protein denaturants (e.g. chaotropic salts) may also denature nucleic acid secondary structure in addition to denaturing cells and proteins. Numerous protein denaturants are known in the art and may be selected for use in the compositions and methods described herein. Without intending to be limited to a particular protein denaturant, exemplary protein denaturants include guanidinium thiocyanate, guanidinium hydrochloride, sodium thiocyanate, potassium thiocyanate, arginine, sodium dodecyl sulfate (SDS), urea or a combination thereof. Exemplary detergents may be categorized as ionic detergents, non-ionic detergents, or zwitterionic detergents. The ionic detergent may comprise anionic detergent such as, sodium dodecylsulphate (SDS) or cationic detergent, such as ethyl trimethyl ammonium bromide. Non-limiting examples of non-ionic detergent for cell lysis include TritonX-100, NP-40, Brij 35, Tween 20, Octyl glucoside, Octyl thioglucoside or digitonin. Some zwitterionic detergents may comprise 3-[(3-Cholamidopropyl)dimethylammonio]-1-propanesulfonate (CHAPS) and 3-[3-Cholamidopropyl)dimethylammonio]-2-hydroxy-1-propanesulfonate (CHAPS 0).

In one or more embodiments, the protein denaturant comprises a thiocyanate salt. One or more embodiments of the matrix comprises an acid-titrated thiocyanate salt impregnated in a dry state. Exemplary thiocyanate salts include, but are not limited to, guanidinium thiocyanate, sodium thiocyanate, potassium thiocyanate or combinations thereof.

The extraction matrix maintains the stability and integrity of RNA at a desired level after RNA extraction from a biological sample. In one embodiment, the matrix is impregnated with nucleic acid stabilizing reagents. These stabilizing reagents may include RNAse inhibitors, acid-titrated buffer, or chelating agents (e.g EDTA). The composition may further comprise an ultraviolet (UV) inhibitor or a free-radical scavenger.

As noted, the matrix further comprises an RNase inhibitor, wherein the RNase inhibitor comprises vanadyl ribonucleoside complex (VRC), a nucleotide analogue, or a commercially available RNase inhibitor (e.g., SUPERase-In™). The RNAse inhibitor may further comprise pyrophosphate compounds. In one embodiment, sodium pyrophosphate dibasic may be used as an RNase-inhibitor. One or more embodiments of the RNAse inhibitor may further comprise triphosphate salts, such as sodium triphosphate. In one example, addition of sodium pyrophosphate to acid-titrated buffer enhances RNA stability in both liquid state and dry-formats.

Embodiments of the matrix comprise acid or acid-titrated buffer reagents in a dry-state, which may be re-hydrated during extraction of nucleic acids. Examples of the acid include, but are not limited to, acetic acid, citric acid, tartaric acid, phosphoric acid, hydrochloric acid, Tris(2-carboxyethyl) phosphine-hydrochloric acid (TCEP-HCl), oxidized Tris(2-carboxyethyl) phosphine-hydrochloric acid (TCEP-O—HCl), sulfuric acid, nitric acid, vanillic acid, 3-(N-morpholino)propanesulfonic acid, or combinations thereof. As noted, the matrix provides an acidic pH on hydration which extracts and stabilizes the extracted nucleic acids, wherein the hydration may be achieved by adding a sample, water or any other solution (e.g. a buffer solution). One or more embodiments of the matrix provide a pH in a range from 2 to 7 on hydration. In some embodiments, the matrix provides a pH in a range from 3 to 6 on hydration.

Figure 4:
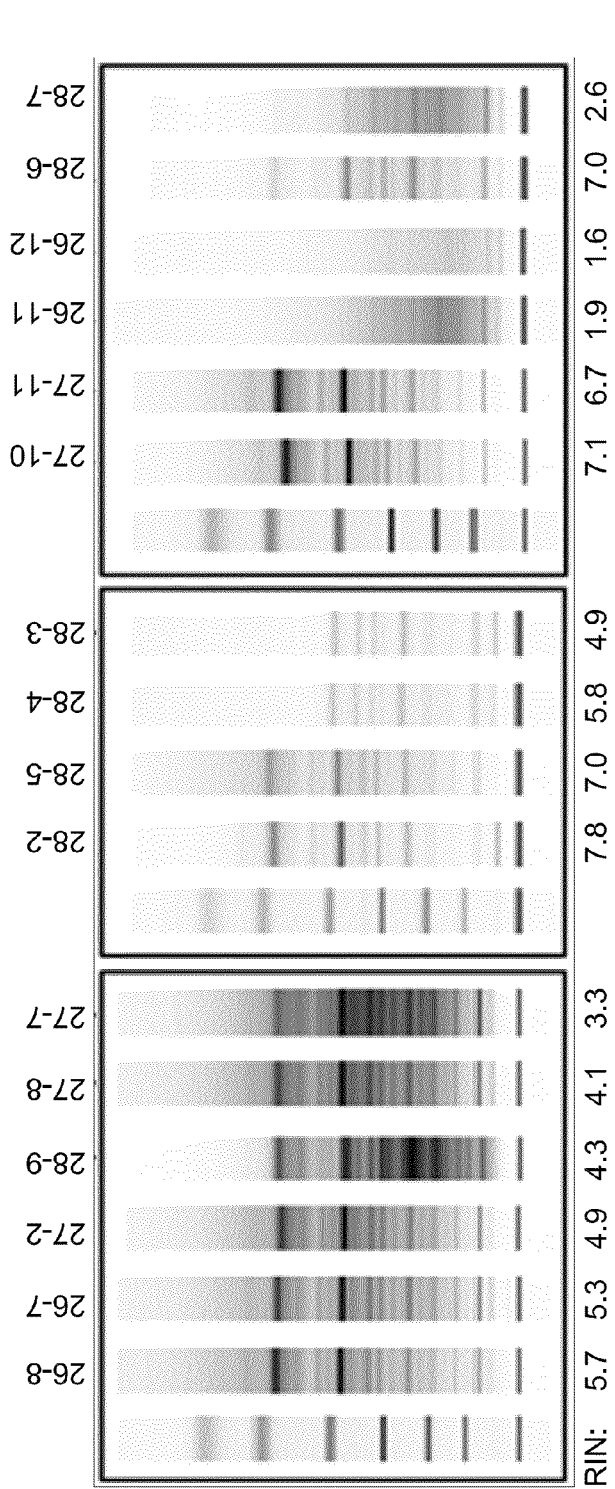
FIG. 4 shows RNA Integrity Numbers (RIN) for dried blood spots collected on various chemically-treated cellulose matrix and stored at ambient temperature for 5, 6, or 12 days prior to RNA analysis on an Agilent 2100 Bioanalyzer.

The extracted nucleic acids, particularly RNA, are stabilized under acidic condition, as shown in Table IV. In one embodiment, the acid-titrated buffer comprises guanidine thiocyanate. At acidic pH from 2 to 7, more particularly at a pH from 3 to 6, a dry-state mixture of guanidine thiocyanate and sodium pyrophosphate in the acidic range on a dry solid matrix stabilizes high-quality RNA in dried blood spots at ambient temperature, as shown by RIN score in FIG. 4. In one embodiment, the acid-titrated buffer comprises guanidine thiocyanate, wherein at acidic pH from 2 to 7, more particularly at pH from 3 to 6, the presence of sodium triphosphate in a dry solid matrix stabilizes high quality RNA, as shown in FIG. 4 by RIN score.

As noted, in some embodiments, the matrix further comprises a UV protectant, a free-radical scavenger, a chelator or combinations thereof. Without intending to be limited to any specific UV protect, an exemplary antioxidants include, for example, hydroquinone monomethyl ether (MEHQ), hydroquinone (HQ), toluhydroquinone (THQ), and ascorbic acid. In some embodiments, the antioxidant is THQ.

In some embodiments, the matrix further comprises at least one reducing agent, wherein the reducing agent is selected from the group consisting of dithiothreitol (DTT), 2-mercaptoethanol (2-ME), tris(2-carboxyethyl) phosphine (TCEP) and combinations thereof.

The extracted nucleic acids comprise ribonucleicacids (RNA), deoxy ribonucleicacids (DNA) or a combination thereof. In one embodiment, the extracted nucleic acids comprise RNA. The RNA may be mRNA, tRNA, rRNA, small RNA, siRNA, miRNA, non-coding RNA, animal RNA, plant RNA, viral RNA or bacterial RNA.

The matrix is configured to store nucleic acids in a dry format at ambient temperature under substantially intact condition. The condition of the RNA refers to the quality of the RNA or integrity of the RNA. The stability and quality of RNA may be assessed on the basis of: quantitative RT-PCR amplification of mRNA targets; the ratio of 28s:18s ribosomal RNA (rRNA), which compromises the bulk of total cellular RNA, and RIN analysis on an Agilent 2100 Bioanalyzer. As noted, RNA quality is determined as a ratio of 28S and 18S ribosomal RNA intensity values, wherein the ratio is calculated by obtaining the intensity of 28S and 18S rRNA by gel electrophoresis of the extracted rRNA followed by ethidium bromide staining. High-quality cellular RNA generally exhibits a 28s:18s rRNA ratio greater than 1. Moreover, high-quality cellular RNA supports efficient amplification of both low-abundance and large (e.g., greater than 1 kB) mRNAs. For the purposes of convenience, rRNA signal intensity and the ratio of 28s:18s rRNA are frequently used to rapidly screen and identify samples with robust RNA storage properties by gel electrophoresis.

As noted, in one embodiment, the RNA quality is determined by capillary electrophoresis of the extracted RNA through a bioanalyzer. As is customary, the RNA quality is quantified as a RIN, wherein the RIN is calculated by an algorithmic assessment of the amounts of various RNAs present within the extracted RNA. High-quality cellular RNA generally exhibits a RIN value approaching 10. In one or more embodiments, the RNA extracted from the dry matrix has a RIN value of at least 4. In some embodiments, the matrix provides for ambient extraction and stabilization of a biosample and produces intact, high quality RNA with a RIN value in a range from 4 to 10, or in one embodiment, the RIN value is in a range from 5 to 8.

An example of a method for extracting and storing nucleic acids from a sample comprises the steps of providing the sample onto a solid matrix comprising a protein denaturant and acid or acid-titrated buffer reagent, generating an acidic pH for extraction of the nucleic acids from the sample upon hydration of the solid matrix with the sample or any externally added liquid, drying the matrix comprising extracted nucleic acids, and storing the extracted nucleic acids on the matrix in a substantially dry state under ambient temperature. Non-limiting examples of the term "providing a sample" include, applying a sample or disposing a sample on the extraction matrix using a pipet, catheter, syringe or conduit. The sample may be poured on the matrix.

The method comprises storing the extracted nucleic acids on the matrix in a dry state at ambient temperature. In some embodiments, the nucleic acids may be stored for more than a one month time period. In some embodiments, the nucleic acids may be stored for more than a six months period. As RNA is generally prone to degradation, the extraction and preservation of RNA using the matrix is useful and may further be used for various downstream applications.

One or more embodiments of the method comprise recovering nucleic acids from the matrix by solid phase extraction technique. In one or more embodiments, the nucleic acids are recovered from the solid matrix by rehydrating the matrix in an aqueous solution, a buffer, or an organic solution, and wherein the nucleic acids are subjected to further analysis. Any method that results in the extraction of nucleic acids, particularly RNA from a sample (e.g., an unpurified biological sample) may be employed. The method delineated above may optionally include a step of washing the matrix before recovering the nucleic acids from the solid matrix for further analysis. For example, the matrix may be washed for one or more times with a suitable buffer or water prior to recovery of the nucleic acids. The nucleic acids may be recovered by rehydrating the solid matrix (e.g., cellulose paper) in an aqueous solution, a buffer solution, as defined above, or an organic solution. In some embodiments, the nucleic acids are recovered from the solid matrix by electroelution.

In one embodiment, a method for extracting and preserving the nucleic acids (e.g., RNA, DNA, or a combination thereof) comprises the steps of: providing a solid matrix, wherein a composition comprises at least one protein denaturant, an acid or acid-titrated buffer reagent, and optionally a free-radical scavenger incorporated into the solid matrix in a dried format; applying a sample (e.g., a biological sample) to the solid matrix to extract the nucleic acids under acidic pH; drying the solid matrix; and storing the nucleic acids on the solid matrix in a substantially dry state at ambient temperature.

In certain examples of the method, the matrix permits the storage of nucleic acids, particularly RNA which is widely known to be an unstable biomolecule to store, in a dry format (e.g., on a solid matrix) at ambient temperatures. The samples utilized in this method include, but are not limited to, biological samples such as blood, serum, tissue, and saliva obtained from any organism, including a human.

EXAMPLE

Reagents: 31-ETF was from GE Healthcare. TCEP was from Soltec Bio Science (Beverly Mass., USA), MOPS was purchased from Aldrich (MO, USA).

Example 1

Preparation of TCEP-O by Oxidation of TCEP

TCEP was oxidized to TCEP-O to analyze the contribution of reducing activity to RNA preservation in dried biosamples.

Approximately 1 gram of TCEP was dissolved in 25 mL of 30% hydrogen peroxide and solution pH was adjusted to 8.0 using sodium hydroxide. The reaction mixture was incubated for 3 hours to complete the oxidation reaction and the products were dried in an oven for subsequent analysis. $P^{31}$ NMR confirmed loss of TCEP in the reaction product relative to a TCEP reference. This oxidation reaction was repeated in the presence of the antioxidant THQ with similar results. The results are set forth in FIG. 1.

Example 2

Confirmation of Loss of Reducing Activity on Dry Matrices Coated with TCEP-O

Paper samples were prepared in solutions containing TCEP or TCEP-O using a simple dip-coating process. Briefly, coating solutions were prepared as described in Table I. Since the control sample, 25-1, resulted in a final solution having pH of 3.5, all other samples were adjusted to pH 3.5 with HCl. 31-ETF cellulose paper was dipped into each coating solution, and after complete saturation, the paper was passed through a nip roller to remove excess solution. Paper samples were then dried in an oven, packaged in Mylar foil bags with desiccant, and stored under 4° C. until use.

TABLE I

Preparation of paper samples containing TCEP or TCEP-O

| Sample | MOPS (mg/mL) | GuSCN (mg/mL) | TCEP (mg/mL) | TCEP-O (mg/mL) | THQ (mg/mL) | Process |
|---|---|---|---|---|---|---|
| 25-1 | 20 | 300 | 10 | | 5 | Prepare MOPS buffer pH 7, add other components, final pH is 3.5 |
| 25-3 | 20 | 300 | | 10 | 5 | Prepare MOPS buffer pH 7, add other components, adjust pH to 3.5 with HCl |
| 27-5 | | 300 | 10 | | | Dissolve GuSCN and TCEP in water, adjust pH to 3.5 with HCl |
| 27-6 | | 300 | | 10 | | Dissolve GuSCN and TCEP-O in water, adjust pH to 3.5 with HCl |

Figure 2:
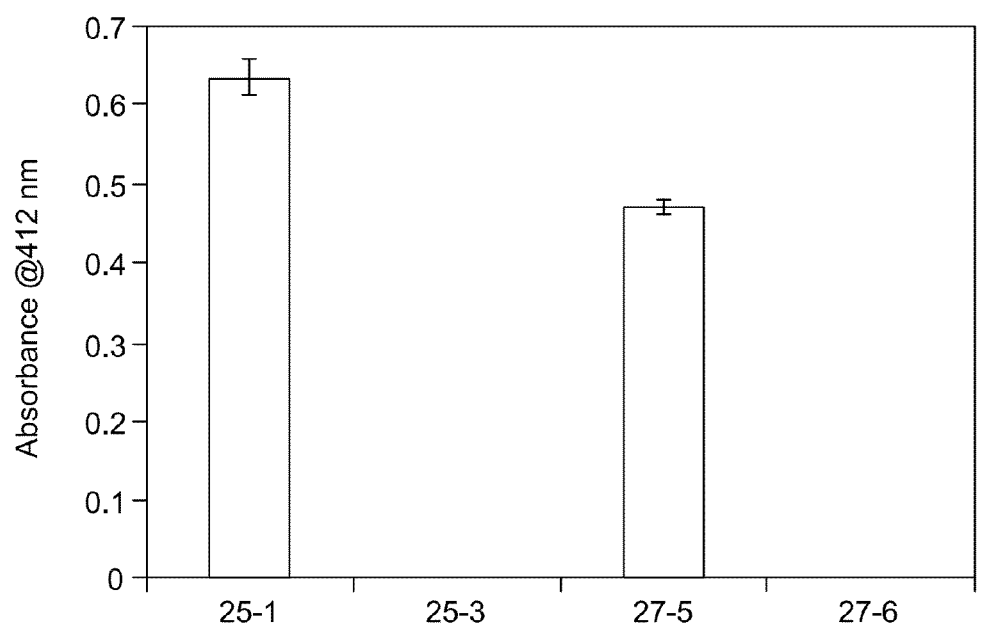
FIG. 2 shows a bar graph derived from a 5,5'-Dithiobis-(2-Nitrobenzoic Acid) (DTNB) colorimetric assay for TCEP and TCEP-O reducing activity on cellulose samples.

Following sample preparation, the reducing activity of the paper was analyzed using a DTNB colometric assay. A 1 mM DTNB working solution was prepared in PBS from a 2.5 mM stock solution in water. Sample punches (with 3 mm diameter) were cored from each paper described in Table I, submerged into 5 mL of DTNB working solution, and shaken for 30 minutes. TNB (thiobis-(2-nitrobenzoic acid) in the resulting solutions were then measured by UV absorbance at 412 nm, which are set forth in FIG. 2. Samples 25-3 and 27-6, containing TCEP-O, showed no reduction of DTNB to TNB, indicating loss of reducing power. Samples 25-1 and 27-5 containing TCEP show strong reducing activity by converting DTNB to TNB using the DTNB colorimetric assay. These results confirmed the prior NMR analyses in Example 1.

Example 3

RNA Stability Analysis from Dried Blood Spots

Samples from Example 2, as described in Table I, were spotted with whole blood and tested for the ability to stabilize RNA at room temperature. 50 μL of rat whole blood was collected from the tail vein of a test animal and spotted onto samples 25-1, 25-3, 27-5, and 27-6. Blood spots were air-dried and stored at ambient room temperature under controlled humidity (~20% RH) for 5 days (25-1, 25-3) or 12 days (27-5, 27-6). RNA was extracted from a 7 mm center punch using RLT lysis buffer (Qiagen) fortified with beta-mercaptoethanol, and purified using conventional silica-membrane spin columns in accordance with protocols known in the art (e.g. Qiagen QIAamp RNA blood kit). Purified RNA was eluted from spin columns with nuclease-free water, and RIN for each of the samples were measured on an Agilent 2100 Bioanalyzer using RNA 6000 Pico LabChips. By convention, RIN >6 is indicative of high quality RNA and is highly desirable for quantitative downstream analyses such as RT-PCR or microarray applications.

Figure 3:
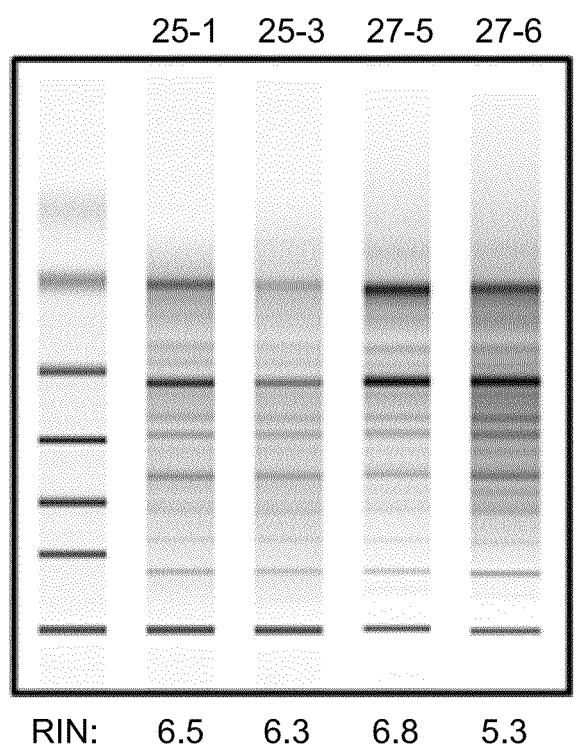
FIG. 3 shows RNA Integrity Numbers (RIN) for dried blood spots collected on chemically-treated cellulose paper containing TCEP or TCEP-O.

As noted, the RIN value was determined by an Agilent 2100 Bioanalyzer using RNA 6000 Pico Lab Chips for each composition listed in Table 1, and the data is shown in FIG. 3. Unexpectedly the samples containing TCEP-O provided comparable RNA integrity to those containing TCEP. RIN scores were only slightly higher in the presence of TCEP (samples 25-1, 27-5) than that of fully oxidized TCEP (samples 25-3, 27-6). This phenomenon may be dependent on acidic pH, since all samples were prepared from coating solutions titrated to at a final pH of 3.5, in order to replicate the natural pH end-point of the control formulation, 25-1, containing TCEP-HCl.

Example 4

Substrate Preparation of Alternative Chemistries at Acidic or Basic pH Profiles

Example 4 was designed to investigate the effects of different mixtures of acid, antioxidant, chaotropic salt, detergent, and pyrophosphate or polyphosphate salts at different solution pH. Paper samples were prepared using the simple dip-coating process described above. Briefly, coating solutions were prepared as described in Table II. 31-ETF cellulose paper was dipped into each coating solution, and after complete saturation the paper was passed through a nip roller to remove excess solution. Paper samples were then dried in an oven and packaged in Mylar foil bags with desiccant until use.

TABLE II

Preparation of paper samples at acidic or basic pH profiles: Acids

| Sample | MOPS (mg/ml) | GuSCN (mg/ml) | SDS (mg/ml) | p-coumaric acid (mg/ml) | Vanillic acid (mg/ml) | Acetic acid (mg/ml) | Citric acid (mg/ml) | Tartaric acid (mg/ml) | Phophoric acid (mg/ml) | Process |
|---|---|---|---|---|---|---|---|---|---|---|
| 26-8 | 20 | 300 | | | 5.5 | | | | | Prepare MOPS buffer pH 7.0, add other components, adjust pH to 3.5 with HCl |
| 26-7 | 20 | 300 | | 3.5 | | | | | | Prepare MOPS buffer pH 7.0, add other components, adjust pH to 3.5 with HCl |
| 27-2 | 20 | 300 | | | | | | | | Prepare MOPS buffer pH 7.0, add other components, adjust pH to 3.5 with HCl |
| 28-9 | 20 | | 20 | | 5.5 | | | | | Prepare MOPS buffer pH 7.0, add other components, adjust pH to 3.5 with HCl |
| 27-8 | | 300 | | | 5.5 | | | | | Dissolve GuSCN and vanillic acid in water, adjust pH to 3.5 with HCl |
| 27-7 | | 300 | | 3.5 | | | | | | Dissolve GuSCN and p-coumaric acid in water, adjust pH to 3.5 with HCl |
| 28-2 | | 300 | | | | 20 | | | | Dissolve GuSCN and acetic acid in water, adjust pH to 3.5 with NaOH |
| 28-5 | | 300 | | | | | | 20 | | Dissolve GuSCN and tartaric acid in water, adjust pH to 3.5 with NaOH |
| 28-4 | | 300 | | | | | 20 | | | Dissolve GuSCN and citric acid in water, adjust pH to 3.5 with NaOH |
| 28-3 | | 300 | | | | | | | 20 | Dissolve GuSCN and phosphoric acid in water, adjust pH to 3.5 with NaOH |

TABLE III

Preparation of paper samples at acidic or basic pH profiles: Poly- and pyrophosphate salts

| Sample | GuSCN (mg/ml) | NaSCN (mg/ml) | Sodium tri-phosphate (mg/ml) | Sodium pyro-phosphate (mg/ml) | Process |
|---|---|---|---|---|---|
| 27-10 | 300 | | 20 | | Dissolve GuSCN and sodium triphosphate in water, adjust pH to 3.5 with HCl |
| 27-11 | 300 | | | 20 | Dissolve GuSCN and sodium pyrophosphate in water, adjust pH to 3.5 with HCl |
| 26-11 | 300 | | 20 | | Dissolve GuSCN and sodium triphosphate in water, adjust pH to 7.2 with HCl |
| 26-12 | 300 | | | 20 | Dissolve GuSCN and sodium pyrophosphate in water, adjust pH to 7.2 with HCl |
| 28-6 | | 206 | 20 | | Dissolve NaSCN and sodium triphosphate in water, adjust pH to 3.5 with HCl |
| 28-7 | | 206 | 20 | | Dissolve NaSCN and sodium triphosphate in water, adjust pH to 7.2 with HCl |

Example 5

RNA Stability Analysis from Dried Blood Spots on Alternative Chemistries

Samples from Example 4, described in Table II and Table III, were spotted with whole blood and tested for the ability to stabilize RNA at ambient temperature. 50 μL of rat whole blood was collected from the tail vein of a test animal and spotted directly onto paper samples. Blood spots were dried and stored at ambient temperature but controlled humidity (~20% RH) for 5, 6 or 12 days. RNA was extracted from a 7 mm center punch into lysis buffer and purified through silica-membrane spin columns in accordance with protocols known in the art. Following purification and elution, RIN were measured on an Agilent 2100 Bioanalyzer using RNA 6000 Pico Lab Chips. A RIN >6 implies high quality RNA and desirable for quantitative downstream analyses such as RT-PCR or microarray applications.

The results of Example 5 are set forth in FIG. 4. It was discovered that acid-titrated chaotropic salt or detergent compositions yielded RNA of reasonable quality from dried blood spots, although certain formulations are preferable over others based on RIN score. For example, samples 28-2 and 28-5 contain guanidium thiocyanate (GuSCN) and showed RIN values of 7.8 and 7.0 at pH 3.5 in acetic acid and in tartaric acid, respectively. The RIN values for acetic acid (7.8) and tartaric acid (7.0) are higher than the same composition in citric acid (sample 28-4, RIN 5.8) and phosphoric acid (sample 28-3, RIN 4.9) at pH 3.5. In particular, the efficacy of pyrophosphate or triphosphate salts showed a clear pH-dependence for stabilizing RNA in the presence of chaotropic agent, with an overall acidic pH providing very high RIN scores. Identical formulations titrated to neutral pH resulted in severe RNA degradation. For example, samples 27-10 and 28-6, coated with either guanidinium thiocyanate (GuSCN) or sodium thiocyanate (NaSCN) and sodium triphosphate at pH 3.5, showed high RIN values of 7.1 and 7.0, respectively, compared to samples 26-11 and 28-7, which contain the same reagents at pH 7.2. Similarly, samples 27-11 and 26-12 contain GuSCN and sodium pyrophosphate and showed RIN values of 6.7 at pH 3.5 and 1.6 at pH 7.2 respectively. The pyrophosphate and triphosphate moieties are generally understood to be small-molecule RNase inhibitors, for which a pH-dependent mechanism of action in dry-states is not intuitive.

Example 6

Correlation of RIN Performance to Solid-Matrix pH

The pH of the solid-matrix using samples from Example 1 (described in Table I), and Example 4 (described in Table II and Table III), were measured and compared to biological RIN performance. To measure solid-matrix pH, 9 punches (7 mm round) were cored from each paper and submerged into 1 mL water. The punches were homogenized into pulp using a high shear lab homogenizer, and the pH of the aqueous phase was determined with pH test strips.

The results of Example 6 are set forth in Table IV. The pH of each dry solid matrix is generally maintained from the original pH of the solution, by which the solid matrices were coated, although certain formulations are preferable over others. Without limiting to a particular theory, the results confirm that solid matrices bearing acidic pH yield RNA of reasonable quality from dried blood spots, as RIN values for RNA samples derived from compositions under acidic pH are greater than or equal to 4 after several days of ambient storage.

TABLE IV

RIN values for different matrix compositions at acidic or basic pH and under ambient conditions

| Sample code | Composition | | | | | pH | | RIN | Ambient storage |
|---|---|---|---|---|---|---|---|---|---|
| | denaturant | buffer | acid | antioxidant | Phosphate salt | Dipping solution | Paper | | |
| 25-1 | GuSCN | MOPS | TCEP-HCL | THQ | | 3.6 | 4 | 6.5 | 5 days |
| 25-3 | GuSCN | MOPS | TCEP-O-HCL | THQ | | 3.6 | 4.5 | 6.3 | 5 days |

TABLE IV-continued

RIN values for different matrix compositions at acidic or basic pH and under ambient conditions

| Sample code | Composition | | | | | pH | | | Ambient storage |
| --- | --- | --- | --- | --- | --- | --- | --- | --- | --- |
| | denaturant | buffer | acid | antioxidant | Phosphate salt | Dipping solution | Paper | RIN | |
| 27-5 | GuSCN | | TCEP-HCL | | | 3.5 | 4 | 5.3 | 12 days |
| 27-6 | GuSCN | | TCEP-O-HCL | | | 3.5 | 4 | 5.3 | 12 days |
| 26-8 | GuSCN | MOPS | Vanillic acid | | | 3.3 | 4 | 5.7 | 5 days |
| 26-7 | GuSCN | MOPS | p-coumeric acid | | | 3.5 | 4.5 | 5.3 | 5 days |
| 27-2 | GuSCN | MOPS | HCl | | | 3.5 | 5.5 | 4.9 | 5 days |
| 28-9 | SDS | MOPS | Vanillic acid | | | 3.3 | 4 | 4.3 | 6 days |
| 27-8 | GuSCN | | Vanillic acid | | | 3.5 | 4 | 4.1 | 5 days |
| 27-7 | GuSCN | | p-coumeric acid | | | 3.5 | 4.5 | 3.3 | 5 days |
| 28-2 | GuSCN | | Acetic acid | | | 3.5 | 5.5 | 7.8 | 6 days |
| 28-5 | GuSCN | | Tartaric acid | | | 3.5 | 4.5 | 7 | 6 days |
| 28-4 | GuSCN | | Citric acid | | | 3.4 | 4.5 | 5.8 | 6 days |
| 28-3 | GuSCN | | Phosphoric acid | | | 3.6 | 5 | 4.9 | 6 days |
| 27-10 | GuSCN | | HCl | | Sodium triphosphate | 3.5 | 5 | 7.1 | 12 days |
| 27-11 | GuSCN | | HCl | | Sodium pyrophosphate | 3.5 | 5 | 6.7 | 12 days |
| 26-11 | GuSCN | | HCl | | Sodium triphosphate | 7.2 | 8 | 1.9 | 6 days |
| 26-12 | GuSCN | | HCl | | Sodium pyrophosphate | 7.2 | 8 | 1.6 | 6 days |
| 28-6 | GuSCN | | HCl | | Sodium triphosphate | 3.5 | 5 | 7 | 6 days |
| 28-7 | GuSCN | | HCl | | Sodium triphosphate | 7.3 | 8.5 | 2.66 | days |

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A solid matrix, comprising:
  at least one protein denaturant; and
  at least one acid or acid-titrated buffer reagent impregnated therein in a dry state;
  wherein the matrix is a non-dissolvable dry solid material and wherein the matrix is configured to provide an acidic pH upon hydration, extract nucleic acids from a sample, and preserve the nucleic acids in a substantially dry state at ambient temperature; and the acid-titrated buffer reagent generates a pH in a range from 3 to 6, wherein the matrix comprises cellulose, cellulose acetate, glass fiber or combinations thereof.

2. The matrix of claim 1 is a solid phase extraction matrix.

3. The matrix of claim 1, wherein the extracted and preserved nucleic acids comprise ribonucleic acids (RNA), deoxy ribonucleic acids (DNA) or a combination thereof.

4. The matrix of claim 1, wherein the extracted and preserved nucleic acids comprise RNA.

5. The matrix of claim 4, wherein the extracted and preserved RNA has an RNA integrity number (RIN) of at least 4.

6. The matrix of claim 1, wherein the acid comprises acetic acid, citric acid, tartaric acid, phosphoric acid, hydrochloric acid, Tris(2-carboxyethyl) phosphine-hydrochloric acid (TCEP-HCl), oxidized Tris(2-carboxyethyl) phosphine-hydrochloric acid (TCEP-O-HCl), sulfuric acid, nitric acid, vanillic acid, 3-(N-morpholino)propanesulfonic acid or combinations thereof.

7. The matrix of claim 1 further comprising a UV protectant, a free-radical scavenger, a chelator or combinations thereof.

8. The matrix of claim 7, wherein the UV protectant or free-radical scavenger is selected from the group consisting of hydroquinone monomethyl ether (MEHQ), hydroquinone (HQ), toluhydroquinone (THQ), and ascorbic acid.

9. The matrix of claim 1 further comprising an RNase inhibitor.

10. The matrix of claim 9, wherein the RNase inhibitor comprises a triphosphate salt, pyrophosphate salt or combinations thereof.

11. The matrix of claim 9, wherein the RNase inhibitor comprises vanadyl ribonucleoside complex (VRC), sodium pyrophosphate, or a commercially available RNase inhibitor.

12. The matrix of claim 9, wherein the RNase inhibitor comprises sodium triphosphate.

13. The matrix of claim 1 further comprising at least one reducing agent.

14. The matrix of claim 13, wherein the reducing agent is selected from the group consisting of dithiothreitol (DTT), 2-mercaptoethanol (2-ME), tris(2-carboxyethyl)phosphine (TCEP), tris(2-carboxyethyl)phosphine hydrochloride (TCEP-HCl)and a combination thereof.

15. The matrix of claim 1, wherein the matrix comprises cellulose, cellulose acetate, nitrocellulose, glass fiber or any combination thereof.

16. The matrix of claim 1, wherein the matrix is porous.

17. The matrix of claim 1, wherein the protein denaturant is selected from a group consisting of guanidinium hydrochloride, guanidinium thiocyanate, sodium thiocyanate, potassium thiocyanate, arginine, sodium dodecyl sulfate (SDS), urea and combinations thereof.

18. The matrix of claim 1, wherein the sample is a biological sample.

19. An RNA extraction matrix comprising:
a protein denaturant comprising a chaotropic agent, a detergent or combinations thereof; and
an acid or acid-titrated buffer reagent impregnated therein in a dry state,
wherein the matrix is a porous non-dissolvable dry material configured to provide a pH in a range from 3 to 6 upon hydration for extracting RNA and stabilizing the extracted RNA with a RIN of at least 4, wherein the matrix comprises cellulose, cellulose acetate, glass fiber or combinations thereof.

20. The matrix of claim 19 further comprising a UV protectant or free-radical scavenger selected from the group consisting of MEHQ, HQ, THQ, ascorbic acid and combinations thereof.

21. An RNA extraction matrix comprising:
a protein denaturant comprising a chaotropic agent, a detergent or combinations thereof;
an acid or acid-titrated buffer reagent; and
an RNase inhibitor comprising a triphosphate salt or pyrophosphate salt impregnated therein in a dry state, wherein the matrix comprises a porous non-dissolvable dry material configured to provide a pH between 3 to 6 upon hydration and stabilize RNA with a RIN value of at least 4, wherein the matrix comprises cellulose, cellulose acetate, glass fiber or combinations thereof.

22. A method for extracting and storing nucleic acids from a sample, comprising:
providing the sample on a dry non-dissolvable solid matrix comprising;
a protein denaturant; and
an acid or acid-titrated buffer reagent;
generating an acidic pH upon hydration for extraction of nucleic acids from the sample, where the acidic pH is in a range from 3 to 6;
drying the matrix comprising the extracted nucleic acids; and
storing the extracted nucleic acids on the matrix in a substantially dry state at ambient temperature, wherein the matrix comprises cellulose, cellulose acetate, glass fiber or combinations thereof.

23. The method of claim 22 further comprising recovering the nucleic acids from the matrix.

24. The method of claim 23, wherein the recovery of the nucleic acids from the matrix comprises rehydrating the matrix in an aqueous solution, a buffer or an organic solution.

25. The method of claim 23, wherein the recovery of the nucleic acids from the matrix comprises electroelution.

26. The method of claim 22, wherein the sample is a biological sample.

27. The method of claim 26, wherein the biological sample comprises blood, serum, tissue, saliva, or cells.

28. The method of claim 26, wherein the sample is a cell extract, a tissue culture cell preparation, an impure nucleic acid or a purified nucleic acid.

29. The method of claim 22, wherein the extracted nucleic acids comprise RNA, DNA or a combination thereof.

30. The method of claim 22, wherein the extracted nucleic acids comprise RNA.

31. The method of claim 30, wherein the extracted RNA has a RIN of at least 4.

32. The method of claim 22, wherein the matrix further comprises a UV protectant, a free-radical scavenger, a chelator or combinations thereof.

33. The method of claim 32, wherein the UV protectant or free-radical scavenger is selected from the group consisting of MEHQ, HQ, THQ, and ascorbic acid.

34. The method of claim 22, wherein the matrix further comprises an RNase inhibitor.

35. The method of claim 22, wherein the matrix comprises a porous cellulose paper.

36. The method of claim 22, wherein the protein denaturant is selected from the group consisting of guanidinium hydrochloride, guanidinium thiocyanate, sodium thiocyanate, potassium thiocyanate, arginine, SDS, urea and combinations thereof.

37. The method of claim 22, wherein the matrix further comprises a reducing agent is selected from the group consisting of DTT, 2-ME, TCEP, TCEP-HCl and a combination thereof.

38. The method of claim 22, wherein the acid comprises acetic acid, citric acid, tartaric acid, phosphoric acid, hydrochloric acid, TCEP-HCl, TCEP-O-HCl, sulfuric acid, nitric acid, vanillic acid, 3-(N-morpholino)propanesulfonic acid or combinations thereof

* * * * *